United States Patent [19]

Sawa et al.

[11] 4,205,156
[45] May 27, 1980

[54] NOVEL IMIDAZOLE-ISOCYANURIC ACID ADDUCTS AND UTILIZATION THEREOF

[75] Inventors: Natsuo Sawa; Tadao Nomoto, both of Nakatado; Keiko Iuchi, Tokushima; Toshihiro Suzuki, Marugame; Shunichi Kawata, Mitoyo, all of Japan

[73] Assignee: Shikoku Chemicals Corporation, Kagawa, Japan

[21] Appl. No.: 5,493

[22] Filed: Jan. 22, 1979

Related U.S. Application Data

[62] Division of Ser. No. 885,948, Mar. 13, 1978.

[30] Foreign Application Priority Data

Mar. 18, 1977 [JP] Japan .................................. 52-30886

[51] Int. Cl.$^2$ ............................................. C08G 59/56
[52] U.S. Cl. .................................... 528/117; 528/118; 528/341; 528/361; 528/362; 528/367; 525/507
[58] Field of Search ............... 528/117, 118, 361, 367, 528/135, 341, 362

[56] References Cited

U.S. PATENT DOCUMENTS

| | | | |
|---|---|---|---|
| 3,635,894 | 1/1972 | Dowbenko et al. ................... | 260/47 |
| 3,746,686 | 7/1973 | Marshall et al. ................ | 260/47 EN |
| 3,989,673 | 11/1976 | Jenkins et al. .................. | 260/47 EN |

*Primary Examiner*—Earl A. Nielsen
*Attorney, Agent, or Firm*—Sherman & Shalloway

[57] ABSTRACT

An imidazole-isocyanuric acid adduct having the following general formula is disclosed:

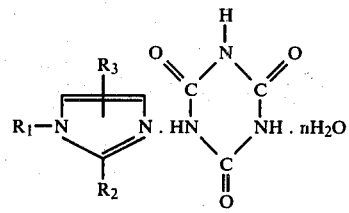

wherein $R_1$ is a member selected from the group consisting of a hydrogen atom, a $\beta$-cyanoethyl group and a $\beta$-[3,5-diamino-S-triazinyl-(1)]-ethyl group, $R_2$ stands for a monovalent hydrocarbon group having up to 17 carbon atoms, $R_3$ is a member selected from the group consisting of a hydrogen atom and an alkyl group having up to 4 carbon atoms, with the proviso that when $R_1$ is a hydrogen atom, $R_2$ is a methyl or phenyl group and $R_3$ is a hydrogen atom and when $R_1$ is a $\beta$-cyanoethyl group, $R_2$ is a phenyl group and $R_3$ is a hydrogen atom, and n is a number of from 0 to 2.

This adduct has peculiar characteristics not possessed by ordinary salts. Namely, the adduct is stable in water, and it decomposes in a solvent or under heating. The adduct is valuable as a curing agent for epoxy resins, and it can be utilized for purification of imidazoles.

8 Claims, 7 Drawing Figures

NOVEL IMIDAZOLE-ISOCYANURIC ACID ADDUCTS AND UTILIZATION THEREOF

This is a division, of Application Ser. No. 885,948, filed Mar. 13, 1978.

BACKGROUND OF THE INVENTION (1) Field of the Invention

This invention relates to a novel imidazole-isocyanuric acid adduct (intermolecular compound) and a process for synthesis thereof. More particularly, the invention relates to an imidazole-isocyanuric acid adduct especially valuable as a curing agent or curing promotor for epoxy resins. Further, the invention relates to an epoxy resin composition comprising a novel imidazole-isocyanuric acid adduct, and also to a process for purification of imidazoles utilizing formation of an imidazole-isocyanuric acid adduct.

(2) Description of the Prior Art

Isocyanuric acid is an industrial chemical which is prepared in large quantities from urea. It is known that this isocyanuric acid provides various salts by reaction with inorganic cations (see, for example, Edwin M. Smolin and Lorence Rapoport, S-Triazines and Derivatives, Interscience Publisher Inc., New York, 1959). However, reactions of isocyanuric acid with organic bases, i.e., amines, are hardly known.

While we were making researches on reactions of isocyanuric acid with various amines, we previously found that isocyanuric acid does not always form stable adducts by reaction with amines irrespective of the kinds of the amines and in other words, isocyanuric acid has such a selectivity to amines that it forms stable adducts with specific amines alone.

BRIEF SUMMARY OF THE INVENTION

We furthered researches and investigations, and found that specific imidazoles described in detail hereinafter provide novel imidazole-isocyanuric acid adducts by reaction with isocyanuric acid, these novel substances have peculiar properties not possessed by ordinary salts in the generic sense of the term, and that by virtue of these peculiar properties, the novel substances can be used effectively and advantageously as curing agents for epoxy resins and for purification of imidazoles. We have now completed the present invention based on these findings.

More specifically, in accordance with the present invention, there is provided a novel imidazole-isocyanuric acid adduct represented by the following general formula:

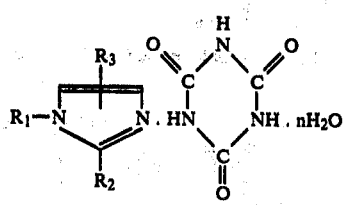

wherein $R_1$ is a member selected from the group consisting of a hydrogen atom, a $\beta$-cyanoethyl group, a benzyl group and a $\beta$-[3,5-diamino-S-triazinyl-(1)]-ethyl group, $R_2$ stands for a monovalent hydrocarbon group having up to 17 carbon atoms, $R_3$ is a member selected from the group consisting of a hydrogen atom and an alkyl group having up to 4 carbon atoms, with the proviso that when $R_1$ is a hydrogen atom, $R_2$ is a methyl or phenyl group and $R_3$ is a hydrogen atom and when $R_1$ is a $\beta$-cyanoethyl group, $R_2$ is a phenyl group and $R_3$ is a hydrogen atom, and n is a number of from 0 to 2. The present invention will now be described in detail.

DETAILED DESCRIPTION OF THE INVENTION

Figure 1:
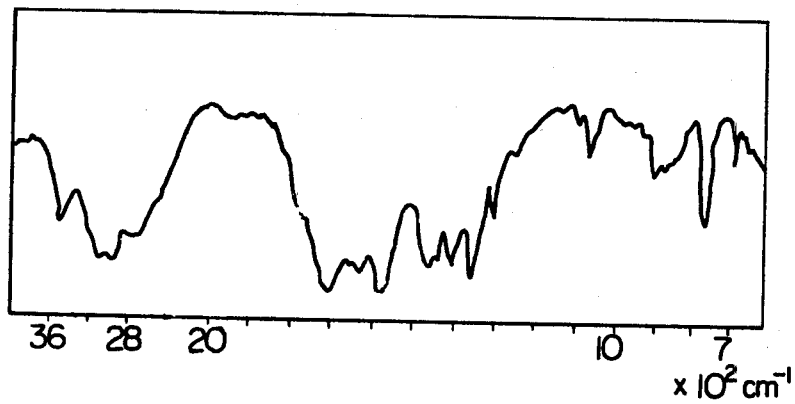

The novel imidazole-isocyanuric acid adduct is represented by the above general formula (1). In this general formula (1), in the case where $R_1$ is a benzyl group or a $\beta$-[3,5-diamino-S-triazinyl-(1)]-ethyl group, $R_2$ may be alkyl and alkenyl groups having up to 17 carbon atoms, such as methyl, ethyl, propyl, butyl, octyl, decyl, undecyl, dodecyl, palmityl, stearyl and oleyl groups, cycloalkyl groups such as a cyclohexyl group, aryl groups such as phenyl, toluyl and ethylphenyl groups, and aralkyl groups such as benzyl and phenetyl groups, and in general, an alkyl group having up to 17 carbon atoms is preferred as $R_2$. In the case where the substituent $R_3$ is an alkyl group having up to 4 carbon atoms, a methyl group is most preferred as $R_3$ but $R_3$ may be an ethyl or propyl group.

The novel imidazole-isocyanuric acid adduct of the present invention, which is represented by the above general formula (1), is prepared by reacting isocyanuric acid with an imidazole compound represented by the following general formula:

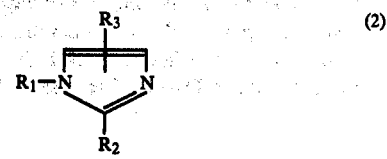

wherein $R_1$, $R_2$ and $R_3$ are as defined above, in a solvent, especially water, dimethylformamide or an aqueous solution of acetic acid.

Any of the imidazole compounds of the formula (2) to be used as the starting compound is a known substance. For example, 2-methylimidazole of the following formula:

and 2-phenylimidazole of the following formula:

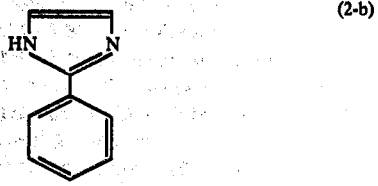

are prepared by forming imidazoline from ethylene diamine and nitrile according to a method as disclosed in Japanese Pat. No. 24965/64 or 1548/67 and subjecting the imidazoline to dehydrogenation according to a method described in Japanese Patent Publication No. 15171/66 or 26405/64.

Further, 1-(β-cyanoethyl)-2-phenylimidazole of the following formula:

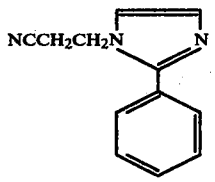
(2-c)

is a compound obtained by addition reaction between 2-phenylimidazole and acrylonitrile (Sawa and Okamura, Journal of the Japanese Chemical Society, 90, 7, pages 704–707).

Imidazole derivatives having a β-[3,5-diamino-S-triazinyl-(1)]-ethyl group, which are represented by the following formula:

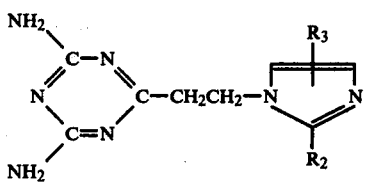
(2-d)

wherein $R_2$ and $R_3$ are as defined above, can readily be synthesized from a corresponding imidazole, acrylonitrile and dicyandiamide according to a method disclosed in Japanese Patent Publication No. 36391/72.

Furthermore, 1-benzylimidazole derivatives represented by the following formula:

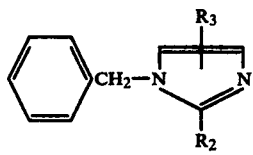
(2-e)

wherein $R_2$ and $R_3$ are as defined above, can easily be prepared by heating a corresponding imidazole and benzyl chloride in an alkali.

In the present invention, in order to obtain the intended imidazole-isocyanuric acid adduct, it is very important that a specific imidazole represented by the above general formula (2) should be selected among various imidazole derivatives.

As pointed out above, isocyanuric acid has a certain selectivity to amines in respect of reaction of forming an adduct with an amine. At the present, a definite interpretation or rule of this selectivity is not established. For example, isocyanuric acid fails to form an adduct by reaction with triethyl amine, N-acetylethylene diamine, β-di-(aminophenyl)-methane or 2-methylimidazoline. On the other hand, isocyanuric acid can form adducts by reaction with ethylene diamine, N-aminoethylethanol amine, benzyl amine and triethylene tetramine. Each of these adducts consists of one molecule of isocyanuric acid and one molecule of the amine.

This selectivity of addition reaction to organic bases in isocyanuric acid is also observed in respect of imidazoles. More specifically, as a result of our researches, it was found that adducts are hardly obtained by reacting isocyanuric acid with the following imidazoles:

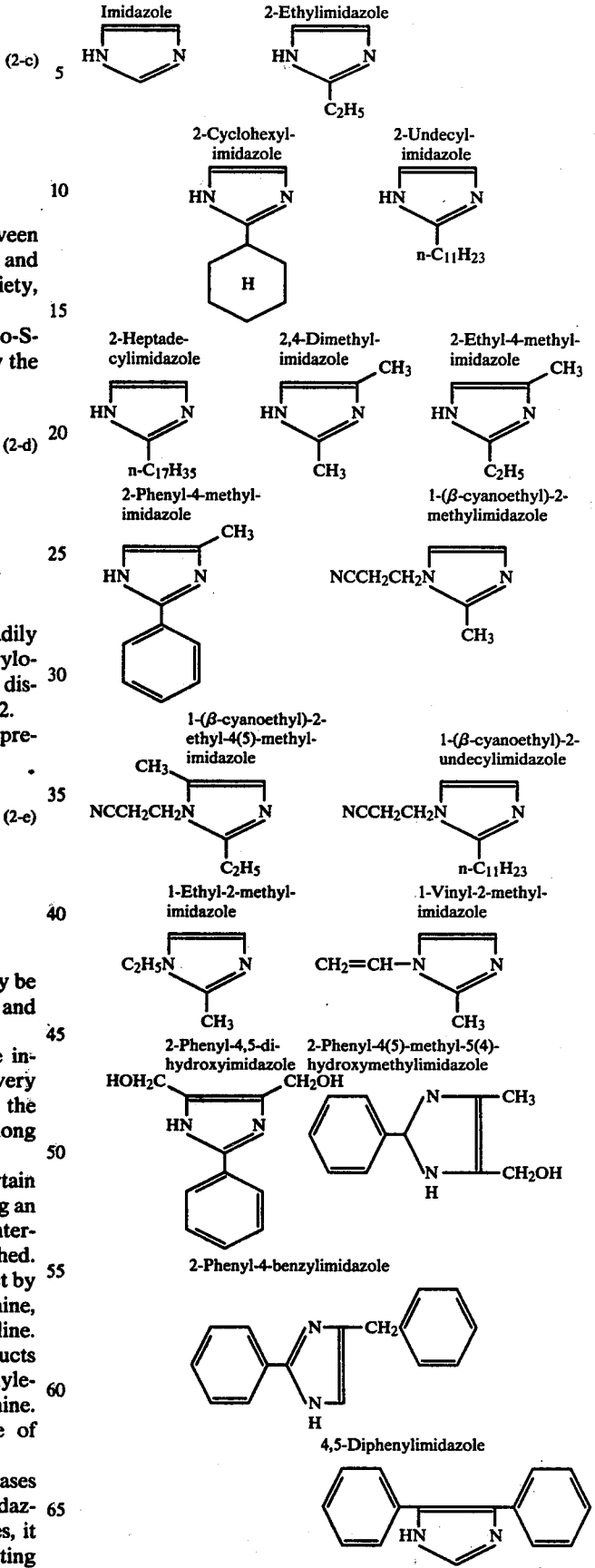

Accordingly, only when specific imidazoles represented by the above formula (2) are selected and used, imidazole-isocyanuric acid adducts can be obtained by reaction with isocyanuric acid.

The addition reaction between the imidazole and isocyanuric acid can easily be carried out by heating both the reactants in a solvent under agitation. It is most preferred that both the reactants be reacted at a substantially equimolar ratio, but even if the molar ratio is changed to some extent from the equimolar ratio, no particular disadvantage is caused. As the solvent, there are preferably employed water, dimethylformamide (DMF) and an aqueous solution of acetic acid.

It is preferred that the reaction be carried out at a temperature approximating to the boiling point of the solvent, generally 100° to 160° C., under reflux at atmospheric pressure. In general, the reaction is completed within 20 minutes to several hours. It is preferred that the solvent be used in such an amount that the reaction mixture takes a homogeneous solution, but this amount is not particularly critical and even if the solvent is used in a smaller amount, no particular disadvantage is caused. Of course, the heating may be accomplished under an elevated pressure, but in this case, the equipment becomes expensive. Accordingly, it is preferred to perform the reaction under atmospheric pressure.

The resulting adduct can easily be isolated by cooling the liquid reaction mixture and recovering precipitated crystals by filtration. The recovered crystals may optionally be purified by customary means such as recrystallization. Water, methanol, DMF and the like may be used as the recrystallization solvent. In some case, an acidic aqueous solution can be used as the recrystallization solvent.

The novel imidazole-isocyanuric acid adduct of the present invention has several peculiar properties not possessed by ordinary salts. These peculiar properties are as follows:

(1) At the developing step in ordinary thin layer chromatography (TLC), the adduct decomposes to the respective constituent components.
(2) The adduct decomposes in a certain solvent to the respective constituent components. It also decomposes by heating to the respective constituent components.
(3) The adduct consists of one molecule of the imidazole and one molecule of isocyanuric acid.
(4) The adduct is very stable to water, and the majority of the adducts can be recrystallized from water.

The above properties (1) and (2) suggest that the imidazole and isocyanuric acid are bonded together through a very weak bonding force. Only in this point, the adduct of the present invention can be clearly distinguished over ordinary normal salts, and it is considered that the adduct is not a salt but a novel adduct.

Characteristic properties of typical imidazole-isocyanuric acid adducts falling within the scope of the present invention will now be described by reference to the accompanying drawing, which illustrates infrared absorption spectra of the imidazole-isocyanuric acid adducts described below.

(a) 2-Methylimidazole-isocyanuric acid adduct:

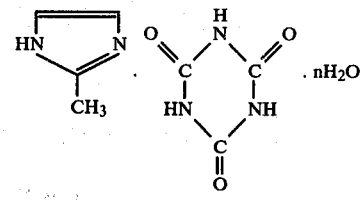

Melting point: higher than 250° C. (W) in case of either $n=15/14$ or $n=1$

In case of either $n=15/14$ or $n=1$, the adduct is in the form of a colorless crystal having the following properties:

Basicity: neutral
Solubility: soluble in hot water (W) and hot DMF but hardly soluble in acetone, methanolf (MeOH) and ethanol (EtOH)
TLC (silica gel, ethanol, $I_2$ coloration): Rf 0.43-0.35 (2-methylimidazole), Rf 0.0 (isocyanuric acid)

The infrared absorption spectrum is as shown in FIG. 1. In FIG. 1, there are observed characteristic absorptions attributed to the respective constituent components, but the spectrum is different from the infrared absorption spectrum of an equimolar mixture of 2-methylimidazole and isocyanuric acid.

Mass spectrum (sample temperature=100° C.; ionizing chamber temperature=215° C.; ionizing energy=75 eV; acceleration voltage=7 KV):
m/e 149, 129 (M+ of isocyanuric acid), 82 (M+ of 2-methylimidazole), 81, 54, 43, 42, 41, 28, 18

A certain amount of the adduct is heated at 50° to 60° C. together with an aqueous solution of HCl for a short time, and the aqueous solution is filtered and the recovered crystal (isocyanuric acid) is weighed. It is confirmed that the adduct consists of 1 molecule of isocyanuric acid and 1 molecule of 2-methylimidazole.

(b) 2-Phenylimidazole-isocyanuric acid adduct:

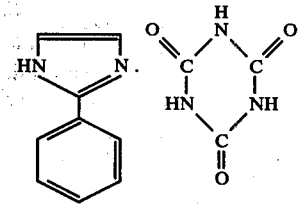

Melting point: 140° C. (partially decomposing) (W)
Form: colorless crystal
Basicity: neutral
Solubility: soluble in hot W and hot DMF, but decomposing to respective components in cold MeOH, EtOH, acetone and $CH_3CN$ and hot toluene
TLC (silica gel, EtOH, $I_2$ coloration): Rf 0.88-0.77 (2-phenylimidazole), Rf 0.0 (isocyanuric acid)

Figure 2:
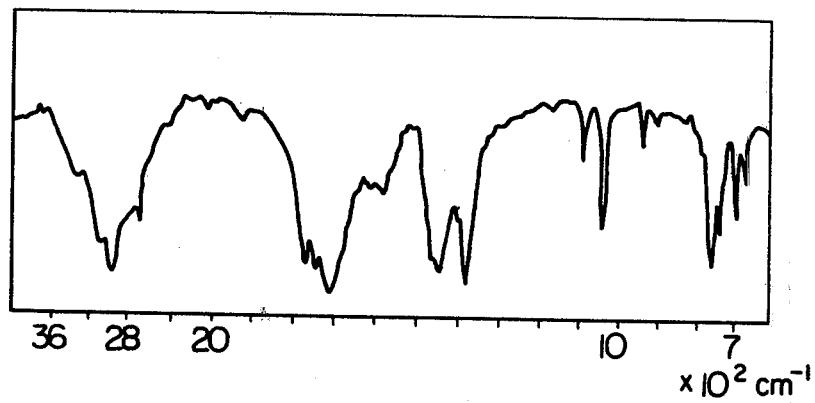

The infrared absorption spectrum of the adduct is as shown in FIG. 2. This spectrum is different from the infrared absorption spectrum of an equimolar mixture of 2-phenylimidazole and isocyanuric acid.

Mass spectrum (sample temperature=170° C.; ionizing chamber temperature=230° C.; ionizing energy=75 eV; acceleration voltage=7 KV):
m/e 149, 144 (2-phenylimidazole), 129 (isocyanuric acid), 118

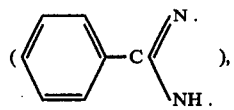

104, 86 (O=C—NH—CO—NH), 70, 44, 43 (O=C—NH), 28

When the adduct is decomposed by an aqueous solution of HCl and isocyanuric acid is recovered by filtration, it is confirmed that the adduct has an equimolar composition.

(c) 1-(β-cyanoethyl)-2-phenylimidazole-isocyanuric acid adduct:

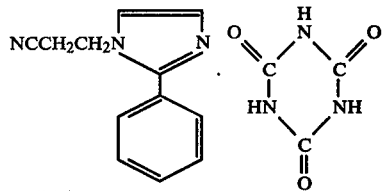

Melting point: 100° C. (decomposing) (W)
Form: colorless crystal
Basicity: neutral
Solubility: soluble in hot W and DMF and decomposing in cold MeOH, EtOH, acetone, $CH_3CN$ and toluene to respective components
TLC (silica gel, EtOH, $I_2$ coloration): Rf 0.70-0.63 [1-(β-cyanoethyl)-2-phenylimidazole], Rf 0.0 (isocyanuric acid)

Figure 3:
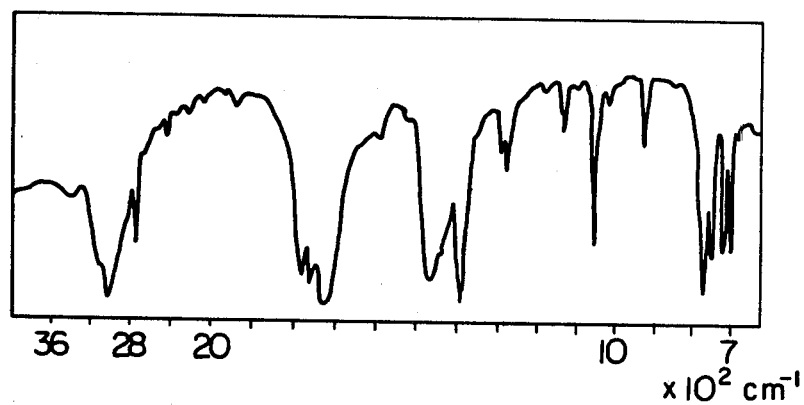

The infrared absorption spectrum is as shown in FIG. 3. The infrared absorption spectrum is different from that of an equimolar mixture of the above imidazole and isocyanuric acid.

Mass spectrum (sample temperature=100° C.; ionizing chamber temperature=220° C.; ionizing energy=75 eV; acceleration voltage=7 KV):

m/e 198, 197 (above imidazole), 196, 169, 157, 156, 149, 144 (2-phenylimidazole), 129 (isocyanuric acid), 117, ... 78, 77, ... 53, 28, ... 18

By using an aqueous solution of HCl, it is confirmed that the adduct has an equimolar composition.

(d) 1-Benzyl-2-methylimidazole-isocyanuric acid adduct:

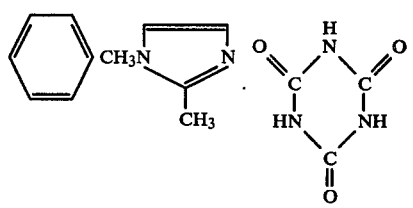

Melting point: 125°-130° C. (partially decomposing) (W)
Form: colorless crystal
Basicity: neutral
Solubility: soluble in hot W and DMF, but decomposing to respective components in cold MeOH, acetone and toluene
TLC (silica gel, EtOH, $I_2$ coloration): Rf 0.5-0.6 (above imidazole), 0.0 (isocyanuric acid)

Figure 4:
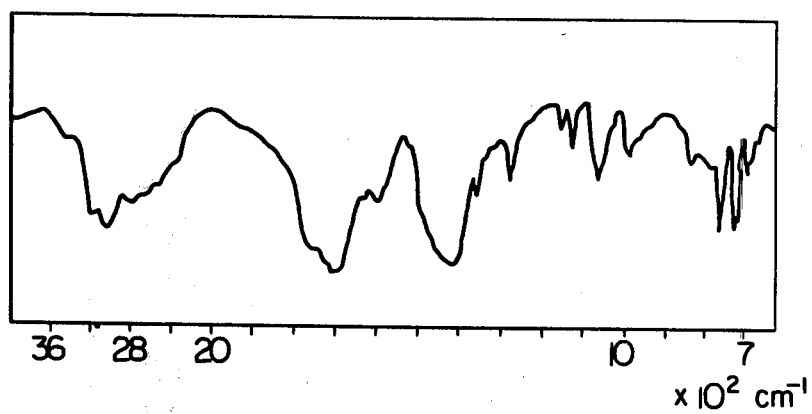

The infrared absorption spectrum is as shown in FIG. 4. The spectrum is different from the infrared absorption spectrum of an equimolar mixture of the above imidazole and isocyanuric acid.

Mass spectrum (sample temperature=70° C.; ionizing chamber temperature=230° C.; ionizing energy=75 eV; acceleration voltage=7 KV):

m/e 172 (above imidazole), ..., 129 (isocyanuric acid), ..., 91 (benzyl group), ..., 77 (phenyl group), ..., 65, ..., 51, ..., 39, ..., 28, ..., 18

By using an aqueous solution of HCl, it is confirmed that the adduct has an equimolar composition.

(e) 2,4-Diamino-6-[2'-methylimidazolyl-(1')]-ethyl-S-triazine-isocyanuric acid adduct:

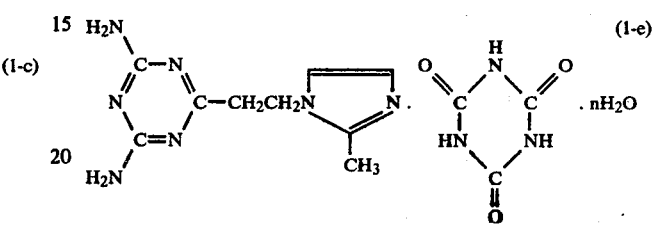

In case of either n=0 or n=2, the adduct has the following properties:
Melting point: higher than 250° C. (W)
Form: colorless crystal
Basicity: neutral
Solubility: soluble in hot W, DMF and methylcellosolv but hardly soluble in MeOH, EtOH, acetone and benzene
TLC (silica gel, EtOH, $I_2$ coloration): 0.2-0.1 (above imidazole), Rf 0.0 (isocyanuric acid)

Figure 5:
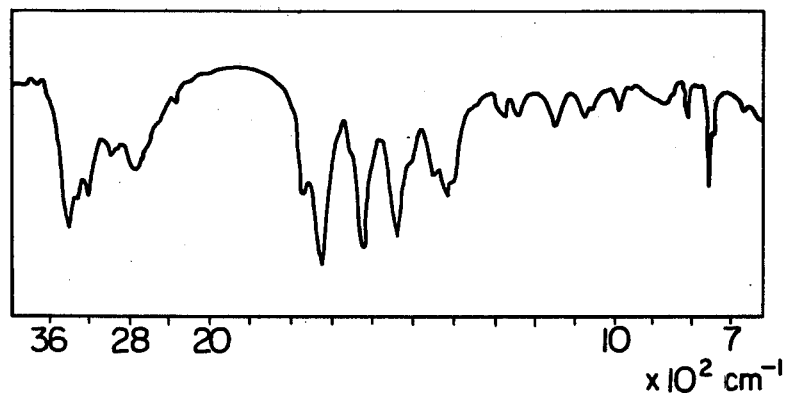

The infrared absorption spectrum is as shown in FIG. 5. The spectrum is different from the infrared absorption spectrum of an equimolar mixture of the above imidazole and isocyanuric acid.

Mass spectrum (sample temperature=110° C.; ionizing chamber temperature=225° C.; ionizing energy=75 eV; acceleration voltage=7KV):

m/e 219 (above imidazole), 149, 138 (imidazolyl ethyl), 129 (isocyanuric acid), ..., 28, 18

By using an aqueous solution of HCl, it is confirmed that the adduct has an equimolar composition.

(f) 2,4-Diamino-6-[2'-undecylimidazolyl-(1')]-ethyl-triazine-isocyanuric acid adduct:

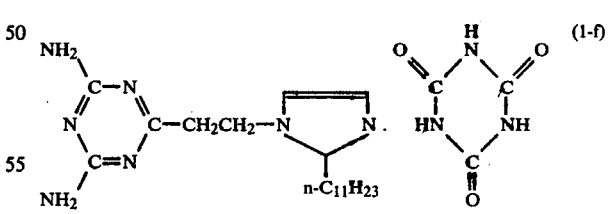

Figure 6:
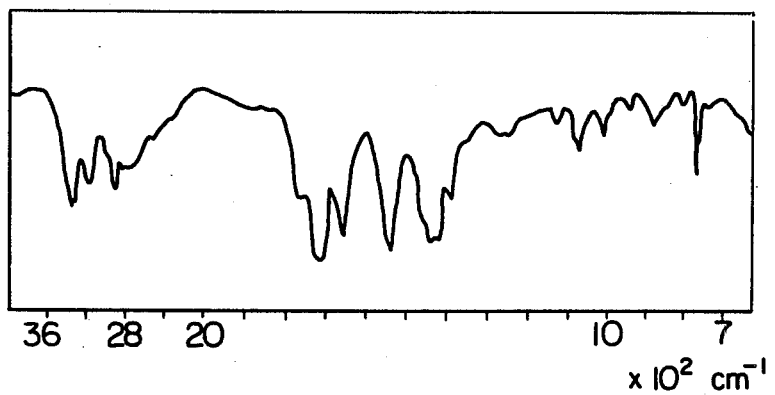

Melting point: higher than 240° C. (MeOH) (partially decomposing)
Form: colorless crystal
Basicity: neutral
Solubility: hardly soluble in W, MeOH, EtOH and acetone The infrared absorption spectrum of the adduct is as shown in FIG. 6, which is different from the infrared absorption spectrum of an equimolar mixture of the above imidazole and isocyanuric acid.

Mass spectrum (sample temperature=150° C.; ionizing chamber temperature=220° C.; ionizing energy=75 eV; acceleration voltage=7 KV):
   m/e 358 (above imidazole), . . . , 232, 219 (2-undecylimidazole-3H), . . . , 138 (triazinyl ethyl), 129 (isocyanuric acid), . . . 82, . . . , 44, 43, . . . , 28, 18

By using an aqueous solution of HCl, it is confirmed that the adduct has an equimolar composition.

(g) 2,4-Diamino-6-[2'-ethyl-4'(5')-methyl-imidazolyl-(1)]-ethyl-S-triazine-isocyanuric acid adduct:

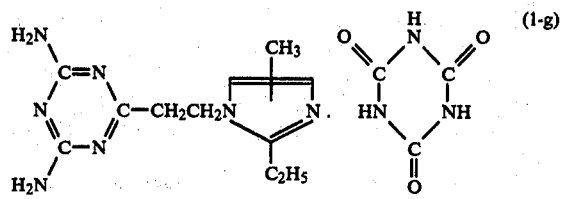

Melting point: higher than 250° C. (W)
Form: colorless crystal
Basicity: neutral
Solubility: soluble in hot W, DMF and methylcellosolv but hardly soluble in MeOH, EtOH, acetone and benzene
TLC (silica gel, EtOH, $I_2$ coloration): Rf 0.2-0.1 (above imidazole), Rf 0.0 (isocyanuric acid)

Figure 7:
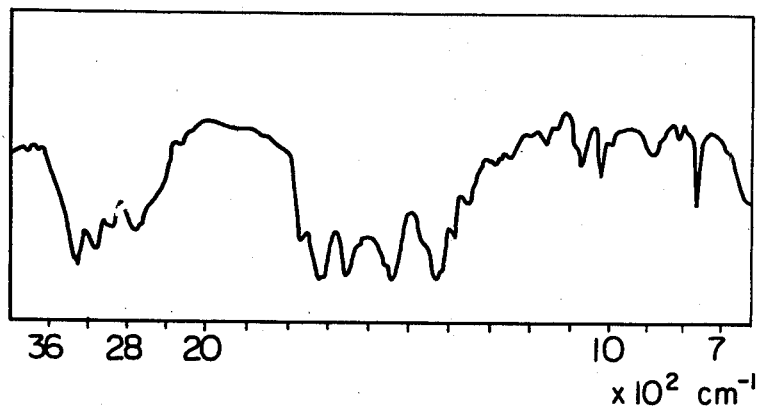

The infrared absorption spectrum of the adduct is as shown in FIG. 7, which is different from the infrared absorption spectrum of an equimolar mixture of the above imidazole and isocyanuric acid.

Mass spectrum (sample temperature=135° C.; ionizing chamber temperature=235° C.; ionizing energy=75 eV; acceleration voltage=7 KV):
   m/e 247 (above imidazole), . . . , 138 (triazinyl ethyl), 129 (isocyanuric acid), . . . , 110 (2-ethyl-4-methylimidazolyl), . . . , 28, 18

By using an aqueous solution of HCl, it is confirmed that the adduct has an equimolar composition.

Synthesis of the imidazole-isocyanuric acid adducts of the present invention will now be described by reference to the following Examples.

EXAMPLE 1

In a stainless steel reaction vessel equipped with a reflux cooler and an agitator, 464 g (5.66 mole) of 2-methylimidazole, 730 g of isocyanuric acid and 16 l of water were boiled under agitation for 1 hour. The reactants were completely dissolved in water. Then, the content was cooled, and the precipitated crystal was recovered by filtration and dried at 80° C. under atmospheric pressure to obtain 895 g of the intended adduct (the yield being 75%). This adduct contained about 15/14 molecules of water of crystallization.

EXAMPLE 2

In a flask equipped with a reflux cooler and an agitator, 32 g (0.39 mole) of 2-methylimidazole, 40 g (0.31 mole) of isocyanuric acid and 660 ml of water were boiled under agitation for about 1 hour. The reactants were completely dissolved in water. Then, the content was cooled, and the precipitated crystal was recovered by filtration, recrystallized from 580 ml of water and air-dried at 80° C. to obtain 51 g of the intended adduct containing about 15/14 mole of water of crystallization (the yield being 78% based on isocyanuric acid). When the adduct was dried at 90° C. under 2 mm Hg for about 1 hour, 1/14 mole of water of crystallization was gradually expelled and the amount of the adduct was reduced to a constant level.

EXAMPLE 3

Under agitation, 22.3 g (0.15 mole) of 2-phenylimidazole, 20 g (0.15 mole) of isocyanuric acid and 200 ml of DMF were refluxed for about 1 hour. The reactants were completely dissolved in DMF. Then, the content was concentrated under reduced pressure, and the residue was recrystallized from 400 ml of water while conducting hot filtration. Air drying gave 30 g of the intended adduct (the yield being 73%).

EXAMPLE 4

In the same manner as described in Example 1, 100 g (0.69 mole) of 2-phenylimidazole, 89 g (0.69 mole) and 1500 ml of water were treated to obtain 141 g of the intended adduct (the yield being 75%).

EXAMPLE 5

In the same manner as described in Example 3, 30 g (0.155 mole) of 1-cyanoethyl-2-phenylimidazole and 20 g (0.155 mole) of isocyanuric acid were completely dissolved in 180 ml of DMF by heating. The reaction mixture was concentrated under reduced pressure, and the residue was recrystallized from 500 ml of water and again from 400 ml of water, and dried to obtain 38 g of the intended adduct (the yield being 76%). The adduct was soluble in water in an amount about 7 to about 8 times the amount of the adduct at 100° C.

EXAMPLE 6

Under heating, 70 g of 1-benzyl-2-methylimidazole and 52.5 g of isocyanuric acid were completely dissolved in 820 ml of water, and the solution was then cooled. The precipitated crystal was recovered by filtration and air-dried to obtain 95 g of the intended adduct (the yield being 77.5%).

EXAMPLE 7

In the same manner as described in Example 3, 22 g (0.1 mole) of 2,4-diamino-6-[2'-methylimidazolyl-(1')]-ethyl-S-triazine, 13 g (0.1 mole) of isocyanuric acid and 50 ml of DMF were heated and refluxed under agitation to form a pasty reaction mixture. Then, the reaction mixture was concentrated under reduced pressure, and the residue was recrystallized from water in an amount about 60 times the amount of the residue and dried at 80° C. under reduced pressure to obtain 26 g of the intended adduct containing 2 molecules of water of crystallization (the yield being 68%).

EXAMPLE 8

Under agitation, 460 g (2.1 moles) 2,4-diamino-6-[2'-methylimidazolyl-(1')]-ethyl-S-triazine, 258 g (2.0 moles) of isocyanuric acid and 8 l of water were heated at 100° to 120° C. for 2 hours to form a pasty reaction mixture. Then, the paste was cooled to 60° to 70° C., and the precipitated crystal was recovered by filtration and dried at 80° C. under 30 mm Hg to obtain 427 g of the intended adduct (the yield being 61.4%).

EXAMPLE 9

The adduct obtained in Example 8 (70 g) was recrystallized from 4.2 l of water (the amount necessary for recrystallization being at least 60 times the amount of the adduct). The recovered crystal was washed with 20 ml of methanol and dried at 80° C. under 30 mm Hg to obtain 61 g of the intended adduct containing 2 molecules of water of crystallization.

EXAMPLE 10

Under agitation, 83.4 g (0.232 mole) of 2,4-diamino-6-[2'-undecylimidazolyl-(1')]-ethyl-S-triazine, 30 g (0.232 mole) of isocyanuric acid and 400 ml of DMF were refluxed for 1 hour to form a pasty reaction mixture. The paste was concentrated under reduced pressure, and extracted with and recrystallized from methanol by using Soxhlet's extractor to obtain 44 g of the intended adduct (the yield being 39%).

EXAMPLE 11

Under agitation, 188 g (0.53 mole) of 2,4-diamino-6-[2'-undecylimidazolyl-(1')]-ethyl-S-triazine, 64 g (0.5 mole), 950 ml of acetic acid and 8550 ml of water were heated at 100° C. for 40 minutes to form a homogeneous solution. Then, the solution was cooled, and the precipitated crystal was recovered by filtration, and extracted with and recrystallized from methanol by using Soxhlet's extractor to obtain 176 g of the intended product (the yield being 70% based on isocyanuric acid).

EXAMPLE 12

Under agitation, 25 g (0.1 mole) of 2,4-diamino-6-[2'-ethyl-4'(5')-methylimidazolyl-(1')]-ethyl-S-triazine, 13 g (0.1 mole) and 50 ml of DMF were heated and refluxed for 1 hour to obtain a pasty reaction mixture. The paste was concentrated under reduced pressure, and the residue was recrystallized from water in an amount about 60 times the amount of the residue to obtain 27 g of the intended adduct (the yield being 71%).

EXAMPLE 13

Under agitation, 80 g (0.324 mole) of 2,4-diamino-6-[2'-ethyl-4'(5')-methylimidazolyl-(1')]-ethyl-S-triazine, 41.8 g (0.324 mole) of isocyanuric acid and 7 l of water were boiled for 1 hour to dissolve the reactants completely in water. The solution was then cooled, and the precipitated crystal was dried at 80° C. under 30 mm Hg to obtain 74 g of the intended adduct (the yield being 61%).

By virtue of the above-mentioned characteristic properties (1) to (4), the novel imidazole-isocyanuric acid adduct of the present invention can be applied to various uses.

First of all, the adduct of the present invention is especially valuable as a curing agent for an epoxy resin.

Imidazole compounds are now used conveniently as intermediate temperature curing agents for ordinary polyepoxy compound, but they still have several defects. For example, the pot life is relatively insufficient and coloration is conspicuous in cured products. Polyepoxy compounds cured by using imidazole compounds are generally excellent in properties. Accordingly, it has been desired in the art to eliminate or moderate these defects involved in imidazole compounds as curing agents.

We found that when the imidazole-cyanuric acid adduct of the present invention is used as a curing agent for a polyepoxy compound, the foregoing defects involved in the conventional imidazole compounds can be removed or remarkably moderated. For example, when the adduct of the present invention is incorporated as a curing agent, there is observed an advantageous phenomenon that the pot life of the resulting polyepoxy composition is extremely prolonged as compared with the case where only the imidazole component constituting the adduct is incorporated. This phenomenon is explainable from the fact that the adduct is neutral. Namely, the electron density of the tertiary nitrogen atom of the imidazole component participating in the curing reaction is remarkably reduced.

On the other hand, when the electron density of the tertiary nitrogen atom is reduced, although the pot life becomes long, there is generally observed a phenomenon that hot curing becomes difficult. For example, when the electron density of the tertiary nitrogen atom of an imidazole compound is reduced by salt-forming reaction with an acid, the pot life can be prolonged but curing becomes difficult at high temperatures. This can be mentioned as a typical instance of the above phenomenon.

In contrast, a polyepoxy composition comprising the adduct of the present invention has a long pot life but there is not caused a phenomenon that hot curing becomes difficult. This characteristic property is explainable from the fact that as pointed out hereinbefore, the adduct of the present invention has such a property that it is readily decomposed under influences of heat into the respective constituent components.

All of the adducts of the present invention represented by the above general formula (1) can be used as curing agents for epoxy resins. Among them, adducts represented by the above formulae (1-a), (1-b) and (1-e) are especially preferred.

This novel curing agent according to the present invention is used in an amount of 1 to 10 parts by weight, especially 3 to 7 parts by weight, per 100 parts by weight of an epoxy resin having more than one epoxy group, i.e., more than one oxirane ring, in one molecule, namely a polyepoxy compound.

In the epoxy resin composition of the present invention, the polyepoxy compound contains more than one epoxy group on the average in one molecule. The epoxy group may be in the form of either

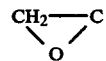

located on the molecule end or

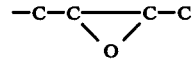

located in the midway of the molecule. The polyepoxy compound may be any of aliphatic, alicyclic, aromatic and heterocyclic polyepoxy compounds. Further, it may be substituted by non-inhibitory groups such as hydroxyl, alkyl, alkoxy, ester, acetal and ether groups.

Most preferred polyepoxy compounds include polyglycidyl ethers of polyhydric phenols such as bisphenol A, bisphenol F, resorcinol, hydroquinone, 4,4-diphenol, dihydroxydiphenylsulfone, phenol-formaldehyde resins and cresol-formaldehyde resins.

Other suitable polyepoxy compounds include glycidyl ethers and glycidyl esters of polyhydric alcohols such as ethylene glycol, propylene glycol, glycerin, trimethylol propane and 1,4-butane diol, polyglycidyl esters of polycarboxylic acids such as phthalic acid, tetrahydrophthalic acid, hexahydrophthalic acid, methylendomethylenetetrahydrophthalic acid, adipic acid and dimer acid, glycidyl amines derived from polyamines such as aniline and 4,4'-diaminodiphenylmethane, epoxidized polyolefins such vinylcyclohexene dioxide, 3,4-epoxycyclohexylmethyl-3,4-epoxycyclohexane-carboxylate and bis-(3,4-epoxy-6-methylcyclohexylmethyl)-adipate, and epoxidized vegetable oils.

The epoxy resin composition of the present invention may further comprise, if desired, a pigment, a plasticizer, filler, a reactive diluent composed of a monoepoxy compound such as butyl glycidyl ether, phenyl glycidyl ether or styrene oxide, a solvent and the like according to known recipes.

A curing agent composed of the novel imidazoleisocyanuric acid adduct of the present invention for epoxy resins may be used singly or in combination with a known curing agent for epoxy resins.

It was found that when the imidazole-isocyanuric acid adduct of the present invention is combined with dicyandiamide and used as a curing agent for epoxy resins, various advantages can be attained in respect of the pot life and curing conditions. When dicyandiamide alone is used as a curing agent for a polyepoxy compound, a long pot life is attained. Therefore, this compound is broadly used in this field. However, this curing agent is defective in that a high temperature and a long time are requied for completion of curing. When the adduct of the present invention is incorporated as a curing promotor into a polyepoxy compound together with dicyandiamide, the above defect of dicyandiamide as the curing agent can be effectively eliminated, and curing can be accomplished at a lower temperature for a shorter time while retaining a long pot life.

In an epoxy resin composition of this type according to this invention, 1 to 20 parts by weight of dicyandiamide and 0.1 to 10 parts by weight of an imidazoleisocyanuric acid adduct represented by the above-mentioned general formula (1) are incorporated in 100 parts by weight of a polyepoxy compound such as mentioned above.

The effects of the novel adduct of the present invention as a curing agent or curing promotor for epoxy resins will now be described by reference to the following Examples.

In these Examples, the pot life of an epoxy composition was determined according to the following method.

The sample composition was stored at 25°±1° C. During the storage, the viscosity of the composition was gradually elevated. The time required for the viscosity to increase to a level 2 times as high as the initial value was defined as the pot life.

Further, in these Examples, the gelation time was determined according to the following method.

About ½ g of the sample composition was placed on a hot plate maintained at 150°±0.5° C. and the composition was spread by a metallic spatula so that the composition covered an area of 2 to 3 cm$^2$. The composition was uniformly pressed and kneaded by the spatula while reciprocating the spatura at an interval of about 2 seconds. The time required to convert the composition to such a state that when the spatula was lifted up, threading did not take place between the composition and the spatula was measured, and this time was designated as the gelation time.

EXAMPLE 14

At room temperature, 100 parts by weight of a polyepoxy compound ("Epikote 828" manufactured and sold by Shell Chemicals) was mixed and kneaded with 5 parts by weight of the 2-methylimidazole-isocyanuric acid adduct prepared in Example 2 by means of a three-roll kneader. The pot life of the so obtained homogeneous composition was 7 days. For comparison, a composition was prepared in the same manner as above except that 5 parts by weight of 2-methylimidazole was used instead of the above adduct. The pot life of the composition was only 3.5 hours. Thus, it was found that the pot life could be remarkably prolonged by using the imidazoleisocyanuric acid adduct.

EXAMPLE 15

A composition was prepared by kneading 100 parts by weight of Epikote 828, 5 parts by weight of the 2-methylimidazole-isocyanuric acid adduct prepared in Example 2 and 3 parts by weight of colloidal silica ("Aerosil #300" manufactured and sold by Nippon Aerosil) by means of a three-roll kneader. The gelation time of the resulting composition was 1 minute and 35 seconds. The glass transition temperature (as measured according to the method utilizing the temperature dependency of the coefficient of linear expansion) of a cured product obtained by heating the above composition at 80° C. for 2 hours and at 150° C. for 4 hours was 163° C. The cured product was further characterized by a flexural strength of 9.6 Kg/mm$^2$ (as measured according to JIS K-7203), a flexural elasticity of 260 Kg/mm$^2$ (as measured according to JIS K-7203) and a volume resistivity of $7 \times 10^{14}$ Ω-cm (as measured according to JIS K-6911). The cured product had a creamy hue.

For comparison, a composition was prepared in the same manner as above except that 5 parts by weight of 2-methylimidazole was used instead of the adduct. The gelation time was 24 seconds. A cured product obtained by heating this composition at 80° C. for 2 hours and at 150° C. for 4 hours was found to have a glass transition temperature of 163° C. and a volume resistivity of $1.6 \times 10^{15}$ Ω-cm. The hue of the cured product was blackish brown, though the hue of the product cured by the adduct was creamy.

EXAMPLE 16

The pot life of a homogeneous composition consisting of 100 parts by weight of Epikote 828 and 5 parts by weight of a 2-phenylimidazole-isocyanuric acid adduct was 35 hours. The pot life of a composition prepared in the same manner by using 5 parts of 2-phenylimidazole instead of the adduct was 15 hours. Thus, it was confirmed that the pot life was prolonged by the use of the adduct.

EXAMPLE 17

The gelation time of a homogeneous composition consisting of 100 parts by weight of Epikote 828, 5 parts by weight of a 2-phenylimidazole-isocyanuric acid adduct and 3 parts by weight of colloidal silica was 1 minute and 47 seconds. A cured product obtained by heating this composition at 80° C. for 2 hours and at 150° C. for 4 hours was found to have a glass transition temperature of 170° C., a flexural strength of 10.2 Kg/mm$^2$, a flexural elasticity of 278.9 Kg/mm$^2$, a volume resistivity of $4.8 \times 10^{15}$ Ω-cm and an ivory hue. For comparison, a composition was prepared in the same manner by using 5 parts by weight of 2-phenylimidazole instead of the adduct and it was cured under the same conditions as described above. The cured product was found to have a glass transition temperature of 170° C., a flexural strength of 8.9 Kg/mm$^2$, a flexural elasticity of 269.5 Kg/mm$^2$ and a volume resistivity of $1.0 \times 10^{15}$ Ω-cm. The hue of the cured product was dark brown, though the hue of the product cured by the adduct was ivory.

EXAMPLE 18

The gelation time of a homogeneous composition consisting of 100 parts by weight of Epikote 828, 5 parts by weight of a 1-benzyl-2-methylimidazole-isocyanuric acid adduct and 3 parts by weight of colloidal silica was 1 minute. A cured product obtained by heating this composition under the same conditions as described in Example 17 was found to have a glass transition temperature of 170° C., a flexural strength of 7.7 Kg/mm$^2$, a flexural elasticity of 273.4 Kg/mm$^2$ and a volume resistivity of $4.8 \times 10^{15}$ Ω-cm.

EXAMPLE 19

A product obtained by curing a homogeneous composition consisting of 100 parts by weight of Epikote 828, 5 parts by weight of a 1-cyanoethyl-2-phenylimidazoleisocyanuric acid adduct and 3 parts by weight of colloidal silica under the same heating conditions as described in Example 17 was found to have a glass transition temperature of 172° C., a flexural strength of 9.4 Kg/mm$^2$, a flexural elasticity of 272.1 Kg/mm$^2$ and a volume resistivity of $2.1 \times 10^{15}$ Ω-cm.

EXAMPLE 20

The pot life of a homogeneous composition consisting of 100 parts by weight of Epikote 828 and 5 parts by weight of the 2,4-diamino-6-[2'-methylimidazolyl-(1')]-ethyl-S-triazine-isocyanuric acid adduct prepared in Example 8 was 44 days. The pot life of a composition comprising 5 parts by weight of 2,4-diamino-6-[2'-methylimidazolyl-(1')]-ethyl-S-triazine instead of the above adduct was 26 days.

EXAMPLE 21

The gelation time of a homogeneous composition consisting of 100 parts by weight of Epikote 828, 5 parts of the adduct described in Example 20 and 2 parts by weight of colloidal silica was 2 minutes and 10 seconds. A product obtained by curing this composition under the same heating conditions as described in Example 17 was found to have a glass transition temperature of 166° C., a flexural strength of 8.6 Kg/mm$^2$, a flexural elasticity of 268 Kg/mm$^2$ and a volume resisitivity of $1.8 \times 10^{15}$ Ω-cm. For comparison, a composition was prepared in the same manner by using 5 parts by weight of the corresponding triazine instead of the adduct. The gelation time of the composition was 1 minute and 19 seconds. A product obtained by curing this composition under the same heating conditions as in Example 17 was found to have a glass transition temperature of 171° C., a flexural strength of 10.5 Kg/mm$^2$, a flexural elasticity of 269.6 Kg/mm$^2$ and a volume resistivity of $1.8 \times 10^{15}$ Ω-cm.

EXAMPLE 22

The pot life of a homogeneous composition consisting of 100 parts by weight of Epikote 828 and 5 parts by weight of the adduct prepared in Example 9 was longer than 90 days. The pot life of a composition comprising 5 parts by weight of the corresponding triazine instead of the adduct was 26 days.

EXAMPLE 23

The gelation time of a homogeneous composition consisting of 100 parts by weight of Epikote 828, 5 parts of the adduct described in Example 22 and 2 parts by weight of colloidal silica was 1 minute and 33 seconds. A product obtained by curing this composition under the same heating conditions as in Example 17 was found to have a glass transition temperature of 156° C., a flexural strength of 12.7 Kg/mm$^2$, a flexural elasticity of 262 Kg/mm$^2$ and a volume resistivity of $7.6 \times 10^5$ Ω-cm. For comparison, a composition was prepared in the same manner by using 5 parts by weight of the corresponding triazine instead of the adduct. The gelation time of the composition was 1 minute and 19 seconds. A product obtained by curing this composition under the same heating conditions as in Example 17 was found to have a glass transition temperature of 171° C., a flexural strength of 10.5 Kg/mm$^2$, a flexural elasticity of 269.6 Kg/mm$^2$ and a volume resistivity of $1.8 \times 10^{15}$ Ω-cm.

EXAMPLE 24

The gelation time of a homogeneous composition comprising 100 parts by weight of Epikote 828, 5 parts by weight of the adduct prepared in Example 12 and 2 parts by weight of colloidal silica was 4 minutes 21 seconds. A product obtained by curing this composition under the same heating conditions as described in Example 17 was found to have a glass transition temperature of 168° C., a flexural strength of 10 Kg/mm$^2$, a flexural elasticity of 273.2 Kg/mm$^2$ and a volume resistivity of $1.1 \times 10^{15}$ Ω-cm. The pot life of a comparative composition including 5 parts by weight of the corresponding triazine instead of the adduct was 18 days, which was about ½ of the pot life of the above composition.

EXAMPLE 25

The gelation time of a homogeneous composition comprising 100 parts by weight of Epikote 828, 10 parts by weight of the adduct prepared in Example 11 and 2 parts by weight of colloidal silica was 2 minutes 18 seconds. A product obtained by curing this composition under the same heating conditions as described in Example 17 was found to have a glass transition temperature of 142° C., a flexural strength of 12 Kg/mm$^2$, a flexural elasticity of 260 Kg/mm$^2$ and a volume resistivity of $1.9 \times 10^{15}$ Ω-cm. A product obtained by curing a comparative composition including 10 parts of the corresponding triazine instead of the adduct under the same heating conditions as in Example 17 was found to have a glass transition temperature of 168° C., a flexural strength of 10 Kg/mm$^2$, a flexural elasticity of 255 Kg/mm$^2$ and a volume resistivity of $3.8 \times 10^{15}$ Ω-cm.

EXAMPLE 26

The gelation time of a homogeneous composition comprising 100 parts by weight of Epikote 828, 8 parts by weight of dicyandiamide, 2 parts by weight of the adduct prepared in Example 9 and 3 parts by weight of colloidal silica was 7 minutes 49 minutes. When this composition was stored at 40° C., even after passage of 50 days, the change of the viscosity was substantially the same as the change of the viscosity observed in a homogeneous composition comprising dicyandiamide alone as the curing agent. For comparison, a composition of the same recipe as above except that the adduct was not included was prepared and the gelation time was examined. It was found that the gelation time of this comparative composition was 2 hours and 26 minutes. Thus, it was confirmed that the adduct had a very high curing-promoting activity.

As pointed out hereinbefore, the novel imidazoleisocyanuric acid adduct of the present invention has such a characteristic property that it decomposes in a certain solvent or under heating into the respective constituent components. By utilizing this characteristic property, it is possible to obtain a pure imidazole by decomposing an imidazole-isocyanuric acid adduct refined by recrystallization.

More specifically, in accordance with the present invention, there is provided a process for the purification of imidazoles, which comprises reacting isocyanuric acid with an impurity-containing compound represented by the following general formula:

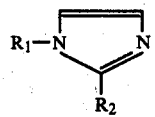

(3)

wherein $R_1$ stands for a hydrogen atom or a benzyl group and $R_2$ stands for a methyl or phenyl group, with the proviso that when $R_1$ is a benzyl group, $R_2$ is a methyl group, in a solvent selected from the group consisting of water, dimethylformamide and an aqueous solution of acetic acid, isolating the formed adduct represented by the following formula:

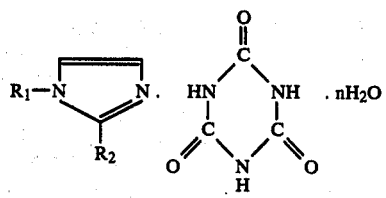

(4)

wherein $R_1$ and $R_2$ are as defined above, and n is a number of from 0 to 2,
and decomposing the so isolated adduct.

The final decomposing step in the above process may be carried out in an organic solvent. Any of organic solvents hardly dissolving isocyanuric acid but readily dissolving the imidazole can be used as the decomposing solvent. As the decomposing solvent that can be conveniently used in the present invention, there can be mentioned, for example, alcohols such as methanol and ethanol, ketones such as acetone, nitriles such as acetonitrile, aromatic hydrocarbons such as toluene and halogenated hydrocarbons such as carbon tetrachloride. In order to dissolve the imidazole compound at a high efficiency while saving the amount used of the solvent, it is preferred that the decomposing step be carried out under heating. Since this decomposition is allowed to advance at low temperatures, the decomposing step may be carried out in the cold state or at room temperature if the use of a large quantity of a solvent is not disliked.

Since the imidazole compounds represented by the above general formula (3) are highly soluble in the abovementioned decomposing solvents, especially methanol and acetone, but isocyanuric acid is hardly soluble in these solvents, when the adducts represented by the above general formula (4) are treated with these solvents, the adducts readily decompose into the imidazole component and isocyanuric acid, and they can easily be separated from each other by filtration.

Decomposition of the adducts of the general formula (4) may also be accomplished by heating. For example, 1-benzyl-2-methylimidazole, 2-methylimidazole and 2-phenylimidazole are readily distillable, and isocyanuric acid adducts of these imidazoles are readily decomposable under heating. Accordingly, if such adduct is heated in a distiller, only the imidazole component can be taken out by distillation. In this case, isocyanuric acid having a high boiling point is not distilled out at all. Thus, the imidazole compounds can be purified effectively according to this process.

Moreover, a purified imidazole can be obtained by decomposing an adduct refined by recrystallization with an acidic solvent, neutralizing the decomposition product and collecting the purified imidazole.

As pointed out hereinbefore, isocyanuric acid has a selectivity in formation of adducts with amines. Accordingly, if the adduct of the present invention is once formed, the proportion of amine type impurities contained in the adduct is very small. There is hardly any chance that amine type impurities are incorporated in the adduct of the present invention. If unfortunately an impurity of an amine of the type capable of forming an adduct with isocyanuric acid is contained in the adduct of the present invention, the adduct can readily be purified by recrystallization.

The purification process of the present invention will now be described in detail by reference to the following Examples.

EXAMPLE 27

1-Benzyl-2-methylimidazole, which is a substance valuable as a curing agent for epoxy resins, is industrially prepared according to a process in which 2-methylimidazole is heated together with benzyl chloride in an aqueous solution of NaOH, the formed oil layer is separated and collected, and the collected oil layer is washed with water and subjected to vacuum distillation. The 1-benzyl-2-methylimidazole always contains small amounts of impurities such as 2-methylimidazole and dibenzyl ether. Since the boiling points of these impurities are very close to the boiling point of the intended product, it is impossible to remove these impurities by distillation. Further, because of the low melting point, it is impossible to remove these impurities from the intended product by recrystallization. The melting point of the 1-benzyl-2-methylimidazole prepared according to the above industrial process is 47° to 51° C., and three peaks (corresponding to 2-methylimidazole, dibenzyl ether and 1-benzyl-2-methylimidazole, respectively) are observed in the gas chromatogram of the product (filler=PEG 6000; column temperature=200° C.). Further, in TLC (silica gel, EtOH), three spots of Rf 0.5–0.6, Rf 0.4–0.3 and Rf 0.2–0.15 are observed. Accordingly, it is seen that the product is impure.

Procedures of Example 6 were repeated by using this 1-benzyl-2-methylimidazole product prepared according to the industrial process to obtain 95 g of a 1-benzyl-2-methyl-imidazole-isocyanuric acid adduct. To 47 g of the so obtained adduct was added 120 ml of methanol, and the mixture was heated and refluxed under agitation for 10 minutes. The reaction mixture was cooled and filtered, and the filtrate was recovered (isocyanuric acid was collected as the residue) and then subjected to concentration under reduced pressure. The concentrate was subjected to expelling distillation under reduced pressure of 2 mm Hg to obtain 1-benzyl-2-methylimidazole having a melting point of 51° to 53° C. in an amount of 25 g (93 mole % based on the starting adduct). The gas chromatogram (under the same conditions as above) of the product showed only one peak, and TLC (under the same conditions as above) of the product showed only one spot of Rf 0.5–0.6. Accordingly, it was found that the product was sufficiently purified.

EXAMPLE 28

The 1-benzyl-2-methylimidazole-isocyanuric acid adduct (30 g) described in Example 27 was subjected to expelling distrillation under a reduced pressure of 30 mm Hg in a Claisen flask to obtain 15.9 g (93 mole % based on the adduct) of 1-benzyl-2-methylimidazole having a melting point of 51° to 53° C. The gas chromatogram and TLC of the product were quite the same as those of the product obtained in Example 27.

EXAMPLE 29

2Phenylimidazole is a substance valuable as a curing agent for epoxy resins, and it is prepared on an industrial scale by forming imidazoline from ethylene diamine and benzonitrile according to a method as disclosed in Japanese Patent Publication No. 24965/64 or 1548/67 and dehydrogenating this imidazoline according to a method as disclosed in Japanese Patent Publication No. 15171/66. This product, however, contains 2-cyclohexyimidazole and 2-phenyl-4-benzylimidazole as impurities. These two impurities are formed as a result of hydrogenation and hydrogenating decomposition of once formed 2-phenyl-imidazole. Even if the product is subjected to rectification in a packed column, it is very difficult to remove these impurities completely. Accordingly, an industrial product of 2-phenylimidazole always contains small amounts of the foregoing two impurities. The melting point of this product is 132° to 142° C. and TLC (silica gel, CHCl$_3$/iso-propyl alcohol=9/1) of the product includes three spots of Rf 0.74–0.63, Rf 0.55–0.40 and Rf 0.23–0.12. Accordingly, it is seen that the product is impure.

Procedures of Example 4 were repeated by using this industrial product of 2-phenylimidazole as the starting compound to obtain 141 g of a 2-phenylimidazole-isocyanuric acid adduct. At the hot filtration step, a small amount of 2-phenyl-4-benzylimidazole was recovered as an insoluble solid. To 141 g of the so obtained adduct was added 300 ml of acetone, and the mixture was refluxed for 30 minutes and filtered. The filtrate was dried to solid and the solid was subjected to expelling distillation in vacuo to obtain 48 g of a fractio boiling at 172° C. under 3 mm Hg. TLC (the same conditions as above) of the fraction showed a spot of 2-phenylimidazole at Rf 0.58–0.48 and a slight spot of 2-cyclohexylimidazole at Rf 0.20–0.15. Accordingly, 48 g of the so obtained fraction was recrystallized from 200 ml of acetone to obtain 31 g of 2-phenylimidazole having a melting point of 147° to 150° C. TLC of the product showed only one spot of Rf 0.48–0.60. Accordingly, it was confirmed that the product was sufficiently purified.

EXAMPLE 30

2-Methylimidazole is a substance valuable as a curing agent for epoxy resins and it is prepared on an industrial scale by forming imidazoline from ethylene diamine and acetonitrile according to a method as disclosed in Japanese Patent Pbulication No. 24965/64 or 1548/67 and dehydrogenating this imidazoline according to a method as disclosed in Japanese Patent Publication No. 26405/64. This industrial product, however, contains minute amounts of 2-methylimidazoline and 1-ethyl-2-methylimidazole as impurities. The latter impurity compound is formed by hydrogenating decomposition of 2-methylimidazole at the dehydrogenating step. Even by rectification in a packed column, removal of these impurities is very difficult. Accordingly, this industrial product always contains minute amounts of the foregoing two impurities.

Procedures of Example 1 were repeated by using this industrial product of 2-methylimidazole as the starting compound to obtain 895 g of a 2-methylimidazole-isocyanuric acid adduct. Then, 50 g of the so obtained adduct was subjected to expelling distillation under atmospheric pressure in a Claisen flask, and the distillate was dried at 50° to 60° C. under reduced pressure to obtain 15.5 g of 2-methylimidazole having a melting point of 142° to 144° C. The gas chromatogram (PEG 6000, column temperature=200° C.) of the recovered product showed only one peak, and TLC (silica gel, EtOH) of the product also showed only one spot. Thus, it was confirmed that the product was sufficiently purified.

EXAMPLE 31

To 32 g of the 2-methylimidazole-isocyanuric acid adduct described in Example 30 were added 25.3 ml of 6N HCl and 40 ml of water, and the mixture was agitated at room temperature for 10 minutes. The resulting pasty mixture was filtered, and 25.3 ml of 6N NaOH was added to the filtrate. The mixture was dried under reduced pressure to solid, and 20.6 g of the recovered solid was subjected to expelling distillation under atmospheric pressure. The distillate was dried at 50° to 60° C. under reduced pressure to obtain 9.6 g of 2-methylimidazole having a melting point of 142° to 144° C. The gas chromatogram (the same conditions as in Example 30) of the product showed one peak, and TLC (silica gel, EtOH) of the product showed only one spot. Thus, it was confirmed that the product was sufficiently purified. Incidentally, 19.9 g of isocyanuric acid was recovered at the filtration step.

What is claimed is:

1. An epoxy resin composition comprising (a) 100 parts by weight of an epoxy resin having more than 1 epoxy group in one molecule and (b) 1 to 10 parts by weight of a compound represented by the following general formula:

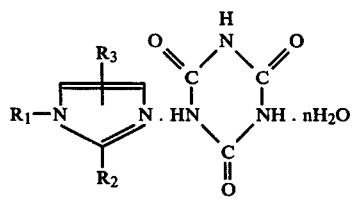

wherein $R_1$ is a member selected from the group consisting of a hydrogen atom, a β-cyanoethyl group, a benzyl group and a β-[3,5-diamino-S-triazinyl-(1)]-ethyl group, $R_2$ stands for a monovalent hydrocarbon group having up to 17 carbon atoms, $R_3$ is a member selected from the group consisting of a hydrogen atom and an alkyl group having up to 4 carbon atoms, with the proviso that when $R_1$ is a hydrogen atom, $R_2$ is a methyl or phenyl group and $R_3$ is a hydrogen atom and when $R_1$ is a β-cyanoethyl group, $R_2$ is a phenyl group and $R_3$ is a hydrogen atom, and n is a number of from 0 to 2.

2. A one-pack type epoxy resin composition comprising (a) 100 parts by weight of an epoxy resin having more than 1 epoxy group in one molecule, (b) 1 to 20 parts by weight of dicyandiamide and (c) 0.1 to 10 parts by weight of a compound represented by the following general formula:

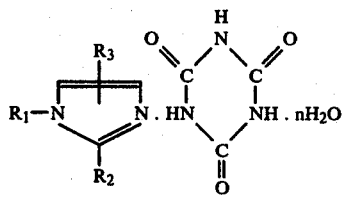

wherein $R_1$ is a member selected from the group consisting of a hydrogen atom, a β-cyanoethyl group, a benzyl group and a β-[3,5-diamino-S-triazinyl-(1)]-ethyl group, $R_2$ stands for a monovalent hydrocarbon group having up to 17 carbon atoms, $R_3$ is a member selected from the group consisting of a hydrogen atom and an alkyl group having up to 4 carbon atoms, with the proviso that when $R_1$ is a hydrogen atom, $R_2$ is a methyl or phenyl group and $R_3$ is a hydrogen atom and when $R_1$ is a β-cyanoethyl group, $R_2$ is a phenyl group and $R_3$ is a hydrogen atom, and n is a number of from 0 to 2.

3. An epoxy resin composition as set forth in claim 1, wherein the compound is an imidazole-isocyanuric acid adduct represented by the following formula:

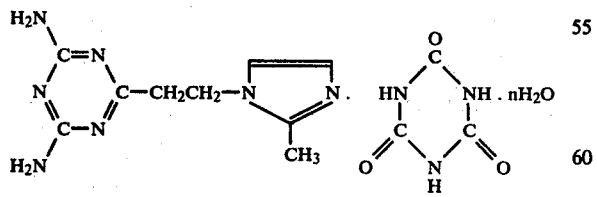

wherein n is a number of from 0 to 2.

4. An epoxy resin composition as set forth in claim 1 wherein the compound is an imidazole-isocyanuric acid adduct represented by the formula:

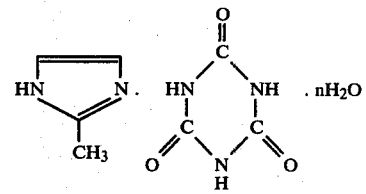

wherein n is a number of from 0 to 2.

5. An epoxy resin composition as set forth in claim 1 wherein the compound is an imidazole-isocyanuric acid adduct represented by the following formula:

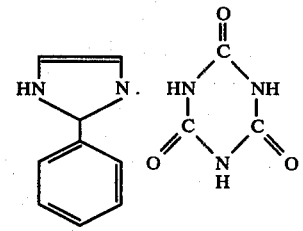

6. A composition as set forth in claim 2 wherein the compound is an imidazole-isocyanuric acid adduct represented by the following formula:

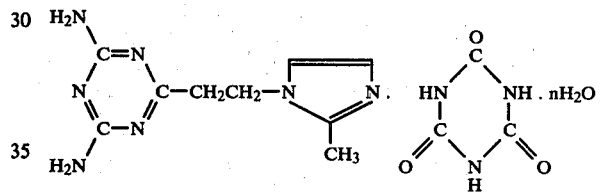

wherein n is a number of from 0 to 2.

7. A composition as set forth in claim 2 wherein said compound is an imidazole-isocyanuric acid adduct represented by the following formula:

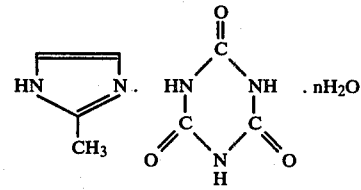

wherein n is a number of from 0 to 2.

8. A composition as set forth in claim 2 wherein said compound is an imidazole-isocyanuric acid adduct represented by the following formula:

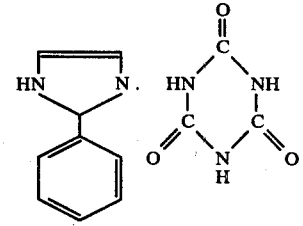

* * * * *